(12) United States Patent
Lauer (10) Patent No.: US 6,814,726 B1
(45) Date of Patent: Nov. 9, 2004

(54) CONNECTOR ELEMENT WITH A SEALING PART

(75) Inventor: Martin Lauer, Auf dem Hollerstock (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/342,017

(22) Filed: Jun. 28, 1999

(30) Foreign Application Priority Data

Jun. 26, 1998 (DE) .......................................... 19828651

(51) Int. Cl.[7] .............................................. A61M 25/16
(52) U.S. Cl. ...................... 604/535; 604/537; 604/905
(58) Field of Search .................... 604/523, 533–539, 604/246, 29, 256, 411, 905, 412–414; 285/2, 3, 21.1, 33, DIG. 2, DIG. 16; 141/311, 329

(56) References Cited

U.S. PATENT DOCUMENTS

| | | | |
|---|---|---|---|
| 3,986,508 A | 10/1976 | Barrington | |
| 4,019,512 A | 4/1977 | Tenczar | |
| 4,030,494 A | 6/1977 | Tenczar | |
| 4,195,632 A | 4/1980 | Parker et al. | |
| 4,508,367 A | * | 4/1985 | Oreopoulos et al. |
| 5,393,101 A | * | 2/1995 | Matkovich |
| 5,492,147 A | * | 2/1996 | Challender et al. |

FOREIGN PATENT DOCUMENTS

| | | |
|---|---|---|
| DE | 28 30 800 | 2/1979 |
| DE | 28 46 677 | 5/1979 |
| DE | 32 10 148 | 9/1983 |
| EP | 0 611 223 | 8/1994 |
| WO | WO 94/08173 | 4/1994 |

* cited by examiner

Primary Examiner—Michael J. Hayes
(74) Attorney, Agent, or Firm—Kenyon & Kenyon (57) ABSTRACT

The present invention relates to a connector element for connecting lengths of tubing, cannulas and catheters to a second connector element. The connector element includes a sealing part that is movable relative to a flow conduit portion of the connector, and which enables the conduit to be sealed with respect to the ambient atmosphere. A sterile connection is therefore ensured.

4 Claims, 8 Drawing Sheets

CONNECTOR ELEMENT WITH A SEALING PART

BACKGROUND OF THE INVENTION

The present invention relates to a connector element for connecting tubes, cannulas and catheters to a second connector element. In particular, the present invention relates to a connector element that provides a sterile connection by remaining sealed with respect to the ambient atmosphere until the connection is made.

DESCRIPTION OF RELATED ART

An important field of applications for connectors is the connection of multiple lengths of tubing, cannulas and catheters, as well as the connection of storage containers to medical working means, such as the connecting ports of a dialysis machine. To minimize any risk to the patient, high demands are placed on the strength and quality of the connectors as well as on maintaining the sterility of the connection to be established. It is important to ensure that there can be no contamination of the components before, during or after the operation of establishing the connection.

U.S. Pat. No. 3,986,508 describes generic connector elements provided with a part sealed before use, to thereby ensure that the portions of the connectors through which media flows remain sealed with respect to the atmosphere and are thus protected from contamination. The sealing parts are inserted into the connector elements to form a seal before use. Then the connector elements are sterilized in a partially assembled state in a heat sterilizer. Following this procedure, the connector elements are joined in such a way that the sealing parts are punctured by a mandrel provided in one of the connector elements, thereby opening a passage for the medium to be conveyed. In this process, the tip of the mandrel first punctures the inside of the sealing part of a connector element and then punctures the adjoining sealing part of the other connector element. One disadvantage of such an arrangement is that any contamination present on the side of the sealing part facing the mandrel could enter the area exposed to the medium once the sealing parts are punctured, and thus the contamination might enter the medium carried through the connector.

SUMMARY OF THE INVENTION

The present invention is directed to a connector element for connecting tubes, cannulas, catheters or other types of fluid lines that substantially obviates one or more of the problems due to limitations and disadvantages of the related art and that has a sealing part that includes a membrane.

Additional features and advantages of the invention will be set forth in the description which follows, and in part will be apparent from the description, or may be learned by practice of the invention. The objectives and other advantages of the invention will be realized and attained by the apparatus and method particularly pointed out in the written description and claims hereof, as well as the appended drawings.

To achieve these and other advantages and in accordance with the purpose of the invention, as embodied and broadly described, the invention is connector element that ensures a sterile connection between the connector element and a second connector element attached to the tube or device to be connected.

The connector element according to the invention has an opening element designed so that the sealing part does not come in contact with the area of the connector used as a conduit for conveying the medium, in either the closed or open position of the sealing part. According to the invention, the opening of the sealing part is not accomplished during the connection operation by contact with the areas or conduits through which the medium passes, but instead through opening elements which are designed and arranged to open the sealing part without allowing it to come in contact with the conduits, either when the sealing part is in the closed, open, or in any intermediary position. In this way, a sterile connection between the two connector elements is always achieved. A sterile connection is also obtained when contaminants might have reached the inside of the sealing part. For example, while establishing the connection, the sealing part is moved in an open position not by a part of the conduit conveying the medium, but instead is opened by a separate opening element, to preclude any contact between the parts of the connector coming in contact with the medium and the sealing part that may be contaminated.

It is especially advantageous if the sealing part includes a base body with a membrane extending over the cross section of the base body. The sealing part can be designed as a cap which is movable relative to the areas for conveying the medium, and its membrane must be opened to allow flow of the fluid during the connection. According to the present invention, the membrane of each connector element is opened by an opening element of the other connector element.

In another preferred embodiment of the present invention, the base body of the sealing part is a cylindrical shell and the membrane is arranged on one end of the base body. The sealing part is advantageously used in such a way that the end area of the base body provided with the membrane of one connection element is oriented away from the "connection side", which is the side of the connector element where the second connector element is inserted. This offers the advantage that a significant portion of the base body protects the membrane from contact, because the membrane is set back from the connection side end portion of the connector element by approximately the length of the base body. It is thus possible to prevent inadvertent contact between the membrane and the opening element of the second connector element.

In a further embodiment of the present invention, the membrane has a straight or cross-shaped slit for the purpose of facilitating opening of the sealing part. This slit is such that the areas for conveying the medium are sealed when the connector elements are disconnected, and only when the connector elements are actuated or joined is the slit opened, to ultimately permit flow through the connector.

According to a preferred embodiment of the present invention, the membrane is a silicone membrane. Such a membrane will close and form a sufficient seal even after slitting, while on the other hand it can easily be folded open and penetrated.

According to another preferred embodiment of the present invention, the conduit for conveying a flowing medium is defined by an inner socket connector. The socket connector borders the parts of the connector element coming in contact with the media, and can be inserted in a fluid-tight manner into the socket connector of another connector element when the connection is established. It is especially advantageous to form the opening element as an outer socket connector, also surrounding the area for conveying the medium.

The area or conduit for conveying the medium and the opening element may be formed by a concentric arrangement of socket connectors, with the outer socket connector which forms the opening element projecting slightly beyond the inner socket connector bordering the area for conveying the medium. This yields a relatively simple arrangement, with the outer of the concentric tubes forming the opening element and the inner concentric tube bordering the area for conveying the flowing medium. According to the present invention, the required opening of the sealing part is achieved by the opening elements, because these are arranged on the outside of the inner socket connectors thereby effecting an opening of the moving sealing part before it comes in contact with the areas exposed to the media. It is also advantageous if the outer socket connector of the opening element projects slightly above the inner socket connector of the area for conveying the medium, or even terminates it. It is essential for the sealing part to be guided or opened in such a way as to prevent contact with the areas for conveying the medium in all stages of movement of the sealing part.

In yet another embodiment of the present invention, the connector element has a housing, with the area for conveying the medium as well as the opening element being accommodated in the housing. It is especially advantageous if an annular gap is formed between the housing and the opening element to accommodate the sealing part when it is moved. Accordingly, the sealing part is guided between the housing and the wall of the opening element while the connection is made, and is moved by the opening element of the second connector element into-a position which causes the sealing part to be opened. At the same time, or subsequently, the sealing part of the second connector element may also be moved back in a corresponding annular gap of the second connector element in an equivalent manner, so that ultimately the areas for conveying the medium of the two connector elements can come in contact with one another without ever being in contact with the inside or outside of the sealing parts.

According to a further preferred embodiment of the present invention, the sealing part can be secured in the housing by a lock. This makes it possible to manufacture the connectors and the sealing parts in two separate operations, to insert the sealing parts into the housing after their manufacture and to secure them in the desired position using the lock. The lock may be constituted of a projection extending away from the housing and a matching recess in the sealing part.

In yet another embodiment of the present invention, the area for conveying the medium can be sealed by a shut-off element. The shut-off element causes fluid-tight sealing of the areas for conveying the medium and can be opened by appropriate penetration elements, when needed, while making the connection. For example, it is thereby possible for the conduit to be filled with liquid from a storage container, up to the shut-off element, before the connection is made.

It is especially advantageous if a penetration body movable relative to the shut-off element is provided and is arranged so that the shut off element can be opened by the penetration body. The penetration body can thus be moved by one of the connector elements during the making of the connection, in such a manner that first the shut-off element of one of the two connector elements to be joined is opened, and then the shut-off element of the other connector element is penetrated, thus permitting flow through the connector.

In another embodiment of the present invention, the area for conveying the medium is formed by an inner socket connector, and the penetration body is arranged in the inner socket connector. Such a connector element is assembled by first inserting the penetration body into the inner socket connector in a suitable position and then inserting the sealing parts. The penetration body may include a projection which can be connected with the inner socket connector of the second connector element. When the projection of the penetration body of one connector element comes in contact with the other connector element while the connection is being established, the penetration body is moved as the connection operation continues, thereby opening the shut-off element.

According to yet another preferred embodiment of the present invention, the shut-off element is designed as an injection molded membrane, preferably made of polypropylene. Due to the use of injection molded membranes, the corresponding areas of the connector elements are hermetically sealed, free of dead space and made of a single material. A particular advantage of using injection molded membranes is the fact that these can be produced together with the other components of the connector element by injection molding in a single operation, thus eliminating subsequent welding of film membranes or subsequent welding or snap assembly of individual components fitted with membranes.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

DETAILED DESCRIPTION OF THE PREFERRED EMBODIMENTS

Figure 1:
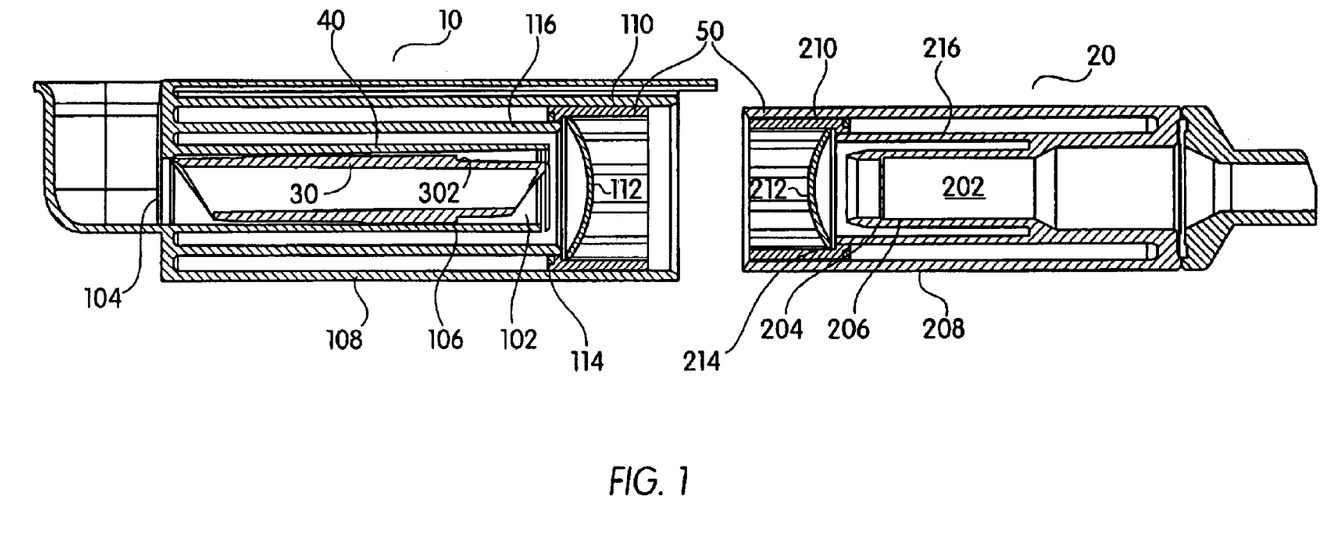
FIG. 1 is a cross section showing two connector elements according to the present invention, in an initial position before the connection.

FIG. 1 shows a sectional diagram of two connector elements 10, 20. Both connector elements 10, 20 have a housing 108, 208 which has a connection for tubing or other working means on one side and a connection opening on the connection side of the connector element. A sealing part 110, 210 is provided on the side of connector elements 10, 20 facing the connection opening. Sealing parts 110, 210 include an essentially cylindrical base body with membranes 112, 212 extending across one end area of the base body. The other end area is advantageously arranged at a distance from the membrane in such a way that an effective protection from contact is assured for the membrane. This result is achieved by having membranes 112, 212 arranged at a distance from the connecting side of the cylindrical base body facing the connection opening.

Base bodies 110, 210 are secured by the first lock 50 in a desired position on housing 108, 208. This offers the advantage that the sealing parts 110, 210 are arranged exactly in the desired position. First lock 50 consists of a projection extending on the inside of the housing 108, 208 and a groove on the outside of the cylindrical base body of sealing parts 110, 210.

An opening element 114, 214 consisting of outer socket connectors 116, 216 is arranged according to the present embodiment in housing 108, 208. Between the outside surface of outer socket connectors 116, 216 and the inside surface of housing 108, 208, there is an annular gap in which the movable sealing part 110, 210 is displaceably accommodated.

Areas or conduits 102, 202 for accommodating a flowing medium are defined by inner socket connectors 106, 206 which extend concentrically with and on the inside of outer socket connectors 116, 216. The portions of outer socket connectors 116, 216 near the connection side define opening elements 114, 214. Conduit 102 of connector element 10, shown on the left in FIG. 1, is sealed by a membrane serving as shut-off element 104. A corresponding shut-off element 204 is also provided in socket connector 206 of connector element 20, shown on the right in FIG. 1.

In the basic position shown in FIG. 1, membranes 112, 212 of sealing parts 110, 210 are closed, forming a tight seal of conduits 102, 202. Thus, corresponding conduits 102, 202 are effectively protected from contamination due, for example, to coughing, and from exposure to unwanted liquid or solid particles.

As FIG. 1 shows, the ends of outer socket connectors 116, 216 project slightly above and beyond inner socket connectors 106, 206. This makes it possible to achieve an opening of membranes 112, 212 with the movement of sealing parts 110, 210 before they come in contact with conduits 102, 202 or with inner socket connectors 106, 206. This ensures that a sterile connection is possible even in the event pathogens or other particles are present on the inside of membranes 112, 212, because a contacting of membranes 112, 212 with conduits 102, 202 and especially, with the end areas of inner socket connectors 106, 206 is effectively prevented according to the present invention.

A penetration body 30 is arranged in socket connector 106 of connector element 10 and is held in a suitable position in socket connector 106 by a second lock 40 disposed in the middle portion of the penetration body 30. Penetration body 30 also has a projection 302 extending from its outside circumference.

Figure 2:
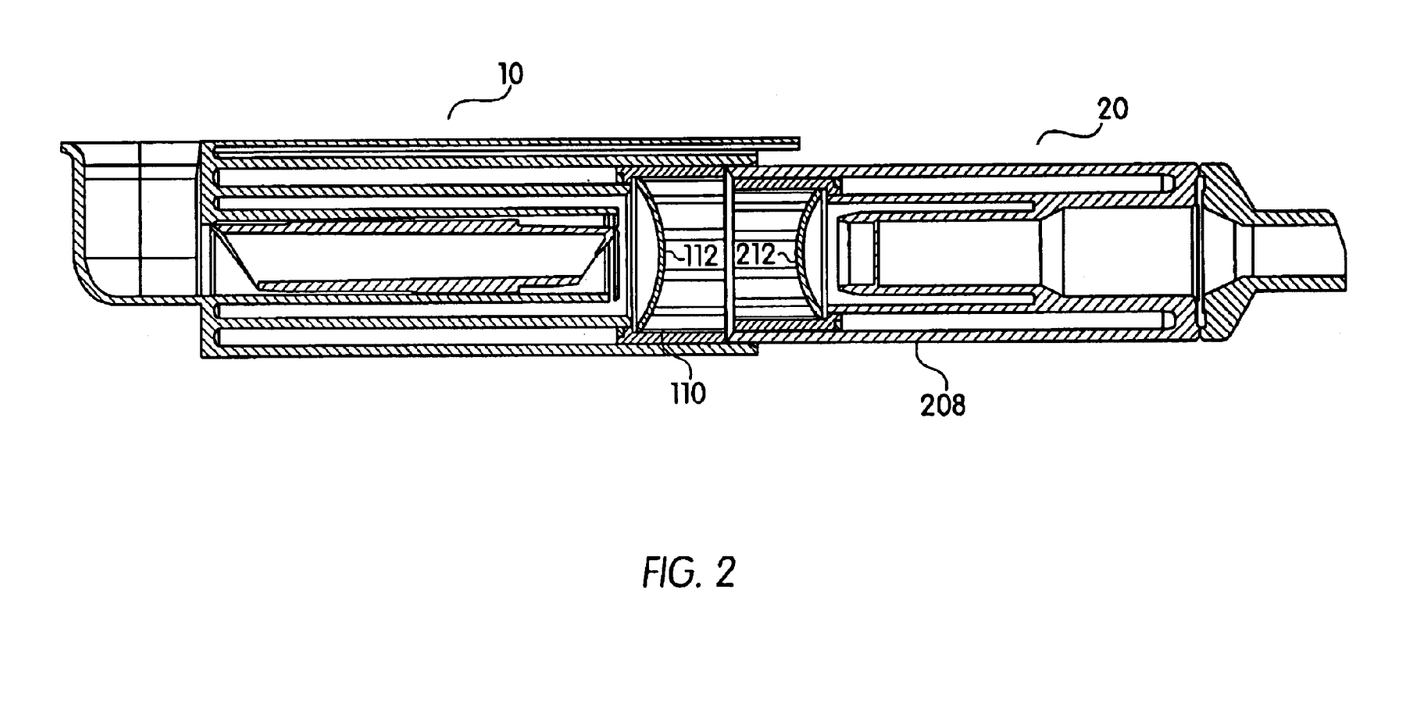
FIG. 2 is a cross section showing the connector elements after inserting the connector element on the right until it comes in contact with the sealing part of the left connector element.

FIG. 2 shows the next step as the connection between connector elements 10, 20 is made. Connector elements 10, 20 according to the present invention are in a position where housing 208 of connector element 20 and sealing part 110 are facing each other and are in contact in their end areas. Up to this point there has not yet been any movement of sealing parts 110, 210, and membranes 112, 212 are still closed.

Figure 3:
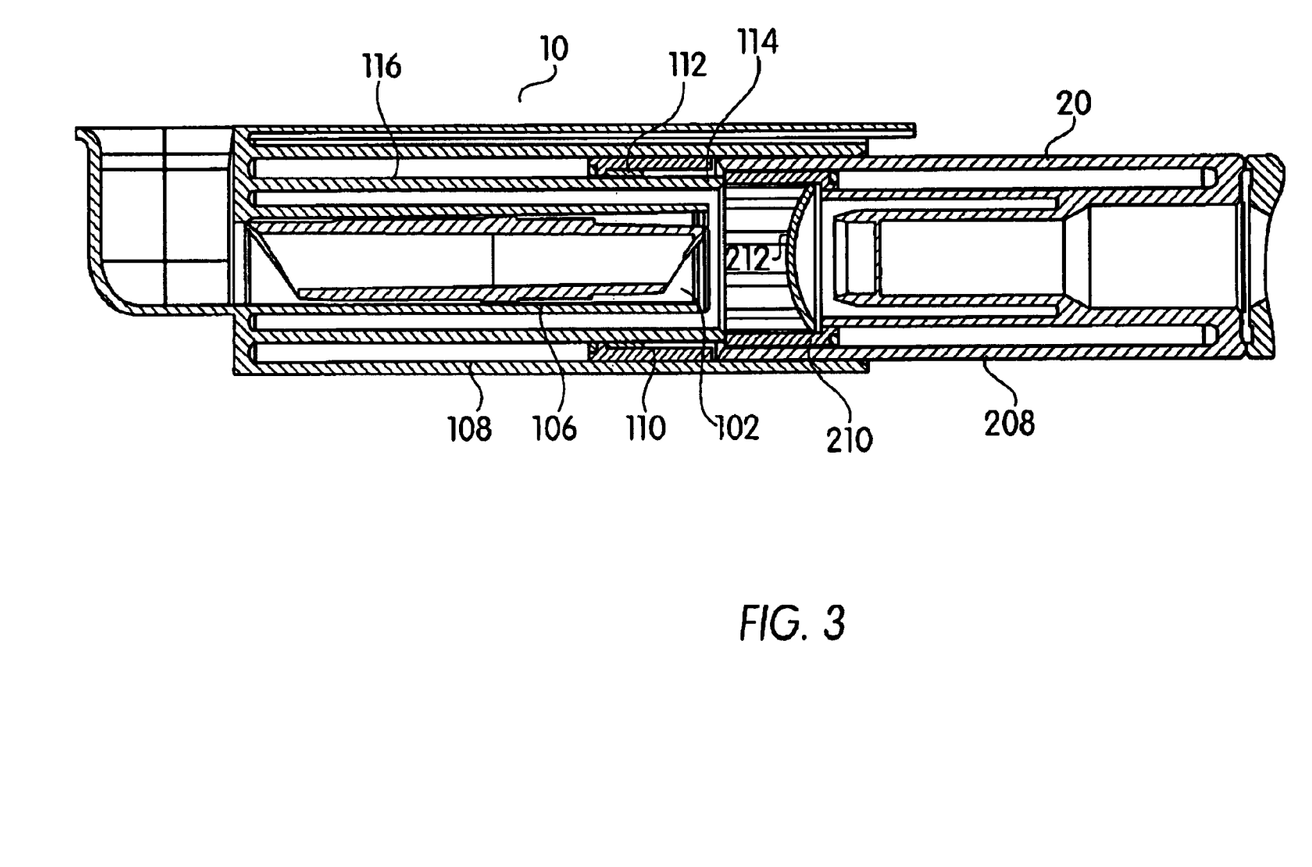
FIG. 3 is a cross section showing the connector elements after opening the sealing part of the connector element shown at the left.

From the position shown in FIG. 2, the connector elements 10, 20 are further pushed together, and FIG. 3 illustrates a condition where connector element 20 has been inserted further into connector element 10. Housing 108 of connector element 10 accommodates housing 208 of connector element 20. Contact of housing 208 with sealing part 110 at the connection side and the movement of connector element 20 causes sealing part 110 to be pushed into the annular gap between housing 108 and socket connector 116 which forms opening element 114. Membrane 112 is kept at a distance from the end area of socket connector 116, so that there can be no contact between those parts at any connection stage. The opened membrane parts are also accommodated in the annular gap without coming in contact with Conduit 102 or socket connector 106 and, in particular, with the end area of socket connector 106 before or during the opening. This reliably prevents contact with membrane 112 and thus contamination of the conduit for conveying media, regardless of whether there is contamination on the inside or outside surfaces of membrane 112.

In the position illustrated in FIG. 3, membrane 112 of sealing part 110 in connector element 10 is already open, while membrane 212 of sealing part 210 in connector element 20 is still closed. The end areas of outer socket connector 116 and of sealing part 210 are in contact with one another in this position.

Figure 4:
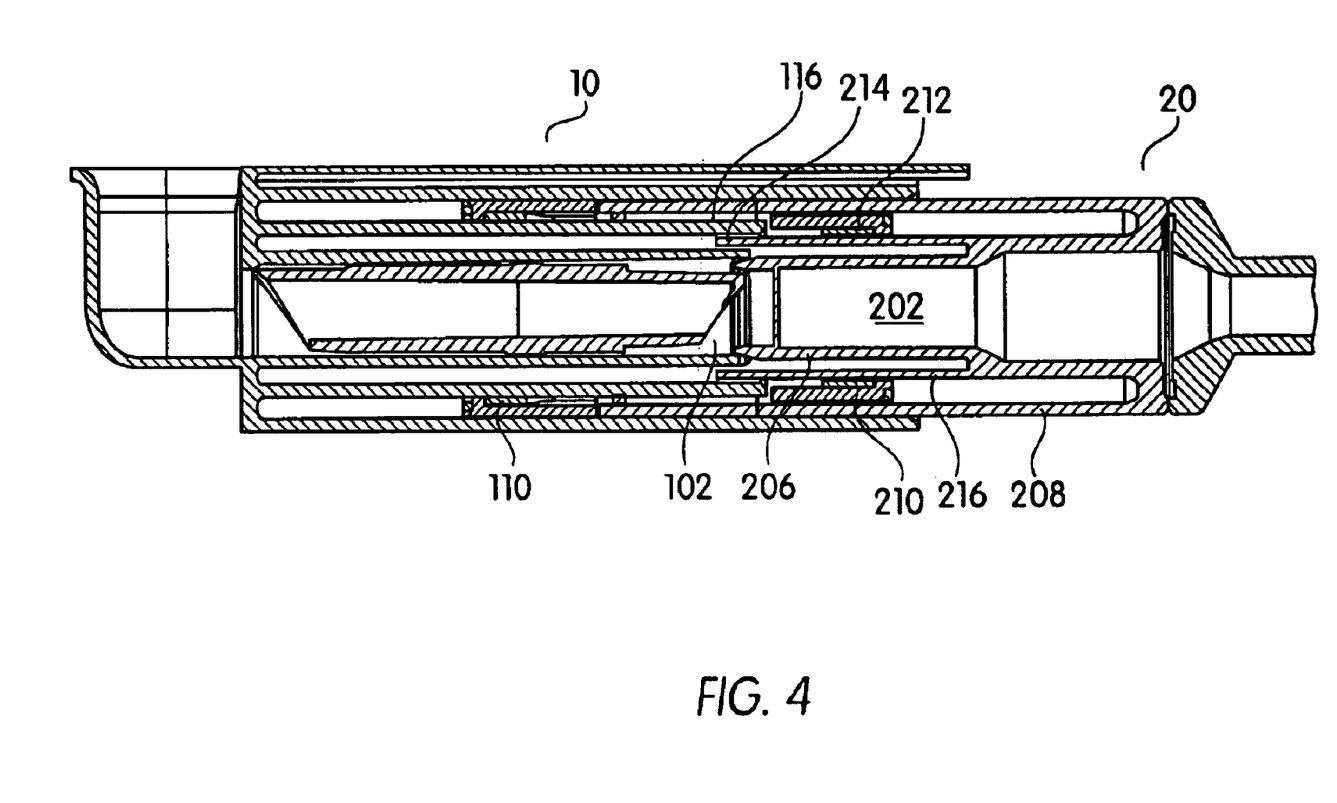
FIG. 4 is a cross section showing the connector elements after opening both sealing parts.

FIG. 4 shows the position of connector elements 10, 20, when connector element 20 has been inserted further into connector element 10, starting from the position illustrated in FIG. 3. This insertion movement results on the one hand in the opened sealing part 110 being pushed further into the annular gap. On the other hand, this movement also results in displacement of sealing part 210 into the annular gap between outer socket connector 216 and housing 208 of connector element 20, due to the contact of outer socket connector 116 with this sealing part 210. In particular, the relative movement of the connector elements leads to membrane 212 of sealing part 210 being opened by the end portion of outer socket connector 216 which defines opening element 214, so that membrane 212 also does not come in contact with the conduits conveying the media, and especially not with the end area of inner socket connector 206 of connector element 20.

This embodiment according to the invention affords the possibility of inner socket connectors 106, 206 coming in contact with one another while at the same time no parts of inner socket connectors 106, 206 or of conduits 102, 202 enter in contact with sealing parts 110, 210 or membranes 112, 212.

FIG. 4 also shows that opening element 214 and inner socket connector 206 of connector element 20 are inserted into the corresponding parts of connector element 10. However, at the same time it is also possible for the inner and outer socket connectors of connector element 10 to be accommodated in the corresponding parts of connector element 20.

Figure 5:
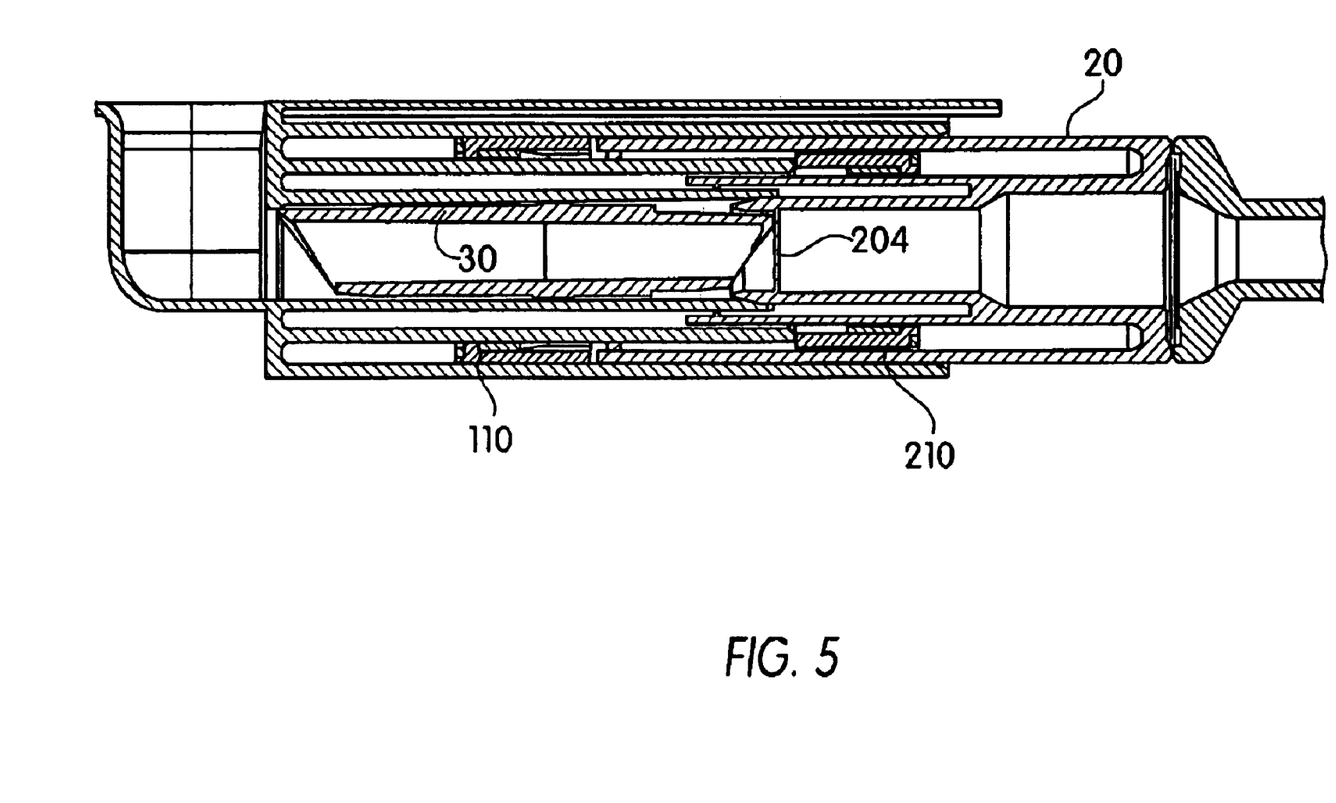
FIG. 5 is a cross section showing the connector elements after further insertion of the connector elements until the membrane of the right connector element comes to rest against the penetration body.

When the connector elements are joined further by pushing them together from the position shown in FIG. 4, the position shown in FIG. 5 is reached, where sealing parts 110, 210 have been inserted further into their respective annular gaps and penetration body 30 is in contact with shut-off element 204 of connector element 20. Shut-off element 204 can be designed as an injection molded membrane, preferably made of polypropylene, and is resistant to all known sterilization methods. Such a membrane not only provides protection against leakage and protection against bacteria but also remains permanently leakproof up to a pressure difference of several bar. In a preferred embodiment of the invention, shut-off element 204 is approximately 0.2 mm thick.

Figure 6:
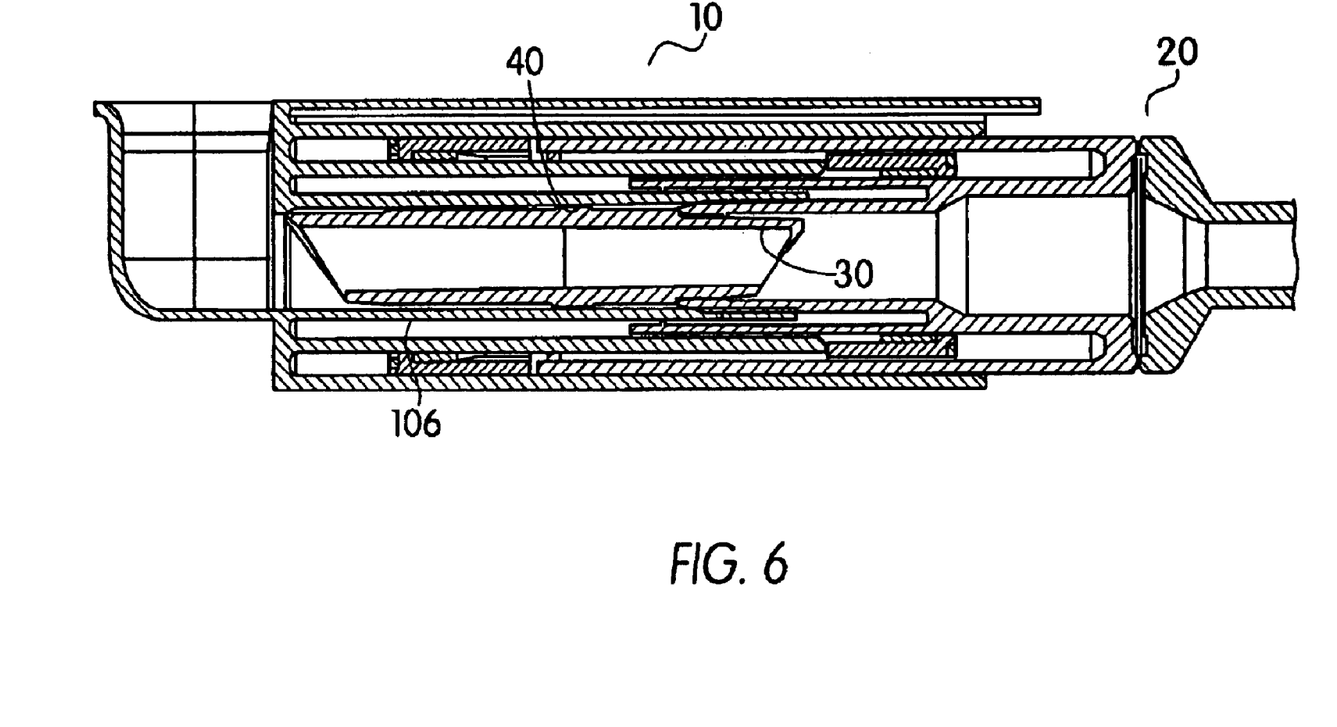
FIG. 6 is a cross section showing the connector elements after opening the shut-off element of the connector element shown at the right.

FIG. 6 shows the position of the two connector elements 10, 20 after the shut-off element 204 has been penetrated by penetration body 30. In a preferred embodiment, penetration body 30 can be an injection molded part which is integrally molded on both sides and is inserted at the time of manufacture into the tube of inner socket connector 106, where it is secured by a second lock 40 to prevent it from falling out. Penetration body 30 can be manufactured very inexpensively in manifold dies, which allows a great deal of latitude in design. In the position shown in FIG. 6, penetration body 30 is still held by second lock 40 in inner socket connector 106 of connector element 10. Second lock 40 is shown in the middle of penetration body 30.

Figure 7:
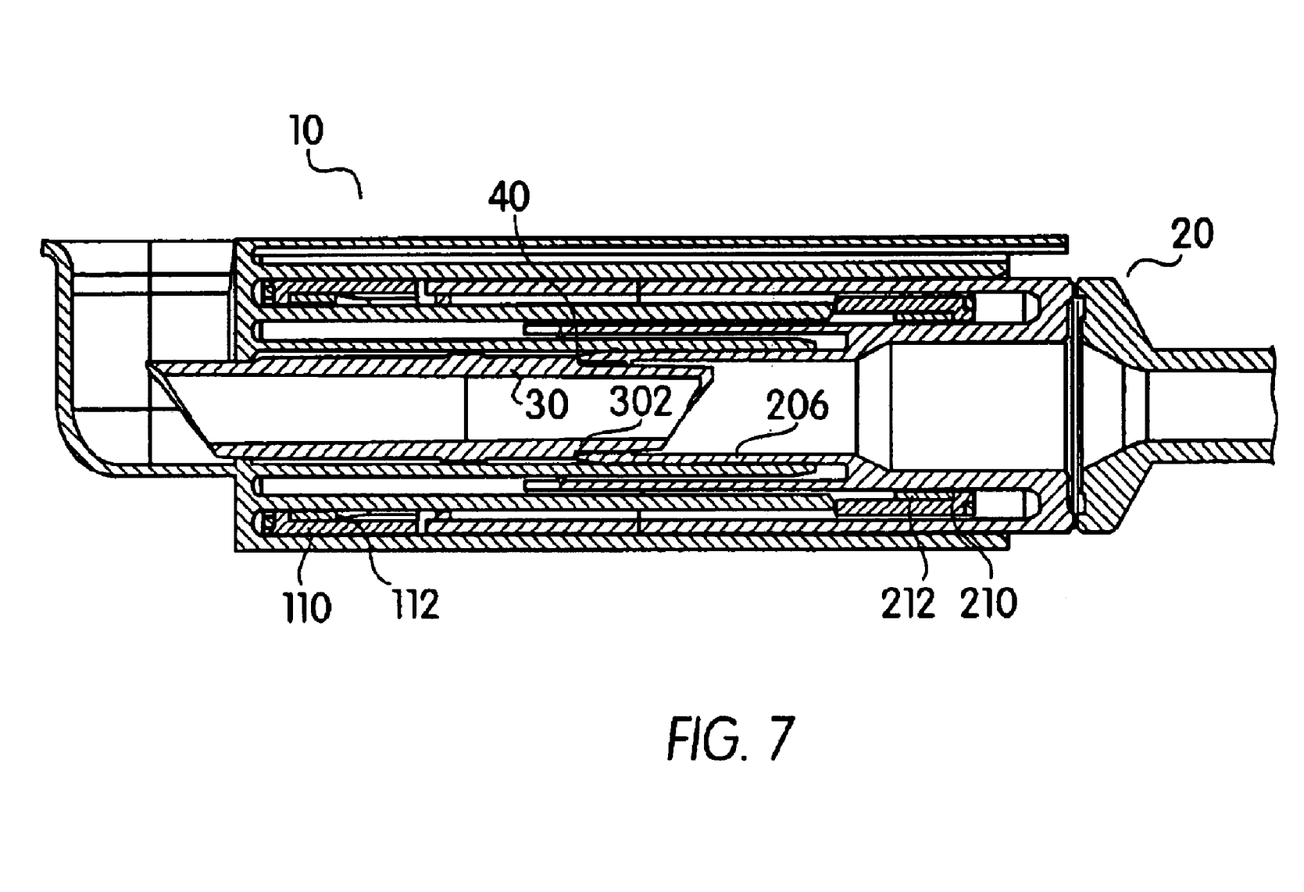
FIG. 7 is a cross section showing the connector elements after opening both shut-off elements.

FIG. 7 shows the final position of the attached connector elements, where penetration body 30 has been moved out of its initial position as held by second lock 40, and has severed the membrane which serves as shut-off element 104. The movement of penetration body 30 is caused by the peripheral projection 302 of the penetration body coming in contact with the end area of inner socket connector 206, so that penetration body 30 is pushed into the position shown in FIG. 7. Penetration body 30 thus has the function of penetrating the two shut-off elements 104, 204 and then widening the openings so that an adequate cross-section is available for flow of the medium.

FIG. 7 also shows that sealing parts 110, 210 and opened membranes 112, 212 are arranged in the end areas of the respective annular gaps. Membranes 112, 212 each consist of a silicone membrane that in a preferred embodiment can be approximately 0.6 mm thick and is produced together with the polyamide injection molding edge in a special two-component injection mold. Typical dimensions of connector element 20 to be inserted include, for example, an outside diameter of approximately 12.6 mm and a depth of penetration of approximately 34 mm. In order for membranes 112, 212 to be able to close again after disconnecting the connector elements, reset elements may be provided to exert a suitable force on sealing parts 110, 210. Such reset elements may be designed for example as springs arranged in the annular gaps between housing 108, 208 and outer socket connectors 116, 216. It is also possible to provide springs which are guided through side slits in the wall adjacent to the annular gap, causing the sealing elements 110, 210 to be returned to a closed position after disconnection of the two connection elements.

The connection system according to the present invention offers the advantage of an initial seal that is tight on the connection sides of both connector elements 10, 20. A safe connecting operation can be carried out whether the connectors are attached to a system filled with liquid or gas. Subsequent connection during disposable use, for example, is also possible. The direction of flow in the connected elements also has no effect on the connection elements.

The connection system according to the invention may be designed as a modular system. Without any changes in dimensions, the connector elements can be manufactured with or without the sealing part, with or without a shut-off element, or partly fitted with sealing and shut-off elements. In the case of disposable connector elements with a high complexity, it may not yet be possible to produce multiple membranes by injection molding in a single operation, due to limits of the current status of polypropylene injection molding technology. It is however possible to use modified designs where polypropylene membranes or elastomer membranes can be subsequently installed at the predetermined locations in a further operation.

Figure 8:
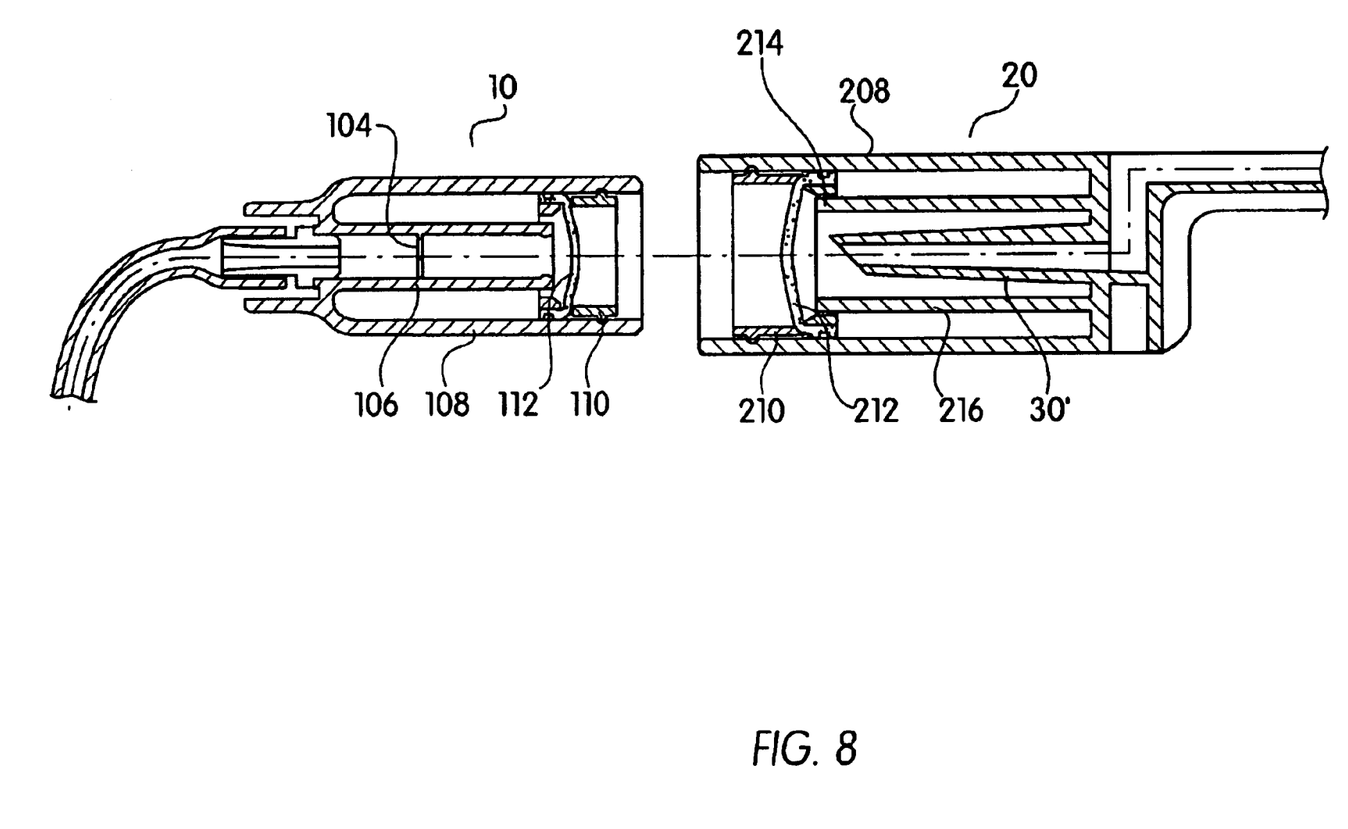
FIG. 8 is a sectional diagram showing the connector elements according to another embodiment of the present invention, having a penetration body designed as a mandrel.

FIG. 8 shows two connector elements 10, 20' that include sealing parts 110, 210 and membranes 112, 212. Connector element 10 has a shut-off element 104 consisting of an injection molded membrane disposed in inner socket connector 106. Shut-off element 104 is opened by mandrel 30' when connector elements 10, 20' are connected, thereby establishing a fluid-tight connection. Mandrel 30' is disposed in connector element 20'.

Before opening shut-off element 104, sealing parts 110, 210 are displaced into the corresponding annular gaps, as described above. These are the annular gap of connector element 10, extending between inner socket connector 106 and housing 108, and the annular gap of connector element 20 extending between housing 208 and opening element 214 formed by outer socket connector 216. When joining connectors 10 and 20, first sealing part 210 is displaced by the housing 108 into the corresponding annular gap, with membrane 212 being opened by the end area of outer socket connector, 216. According to the present invention, mandrel 30' does not come in contact with membrane 212. This offers the advantage that the mandrel 30' can be kept in a sterile condition regardless of any contamination present on the inside of membrane 212. Following the partial displacement of sealing part 210, sealing part 110 and its membrane 112 are opened by contact of the end face of sealing part 110 with the end portion of outer socket connector 216. This causes sealing part 110 to be inserted into the annular gap, membrane 112 to be opened, and mandrel 30' to be inserted into socket connector 106 until shut-off element 104 is opened.

In the embodiment illustrated in FIG. 8, sealing parts 110, 210 and membranes 112, 212 are designed preferably as silicone-polyamide composite injection molded parts, with for example the membranes being preferably approximately 1 mm thick, and being punctured subsequently to form a slot or other opening. This arrangement keeps bacteria and contaminants away from the conduit, and resists leakage of fluid up to approximately 0.05 bar of pressure of the fluid. The membrane, however, opens easily when displaced as described above.

In one embodiment according to the invention, connector element 10 may be designed as a delivery connector element connected to a bag, and connector element 20 can be designed as a receiving connector element connected to a disposable component. This layout according to the present invention, prevents contact with a user's fingers due to the set-back arrangement of membranes 112, 212 on both the bag side and on the disposable side. In addition, a hermetically sealed penetration membrane can be provided in the form of shut-off element 104 on the bag side, to seal the conduit until the connection is established.

Connector elements 10, 20 shown in FIG. 8 can include an elastomer-free mandrel connection system. Sealing parts 110, 210 and membranes 112, 212 provide effective protection from contamination due to, for example, coughing, solid or liquid particles, and also provide protection against leakage.

It will be apparent to those skilled in the art that various modifications and variations can be made in the structure and methodology of the present invention, without departing from the spirit or scope of the invention. Thus, it is intended that the present invention cover the modifications and variations of this invention provided they come within the scope of the appended claims and their equivalents.

What is claimed is:

1. A connector element for connecting a fluid line, preferably a length of tubing, cannulas or catheters to a second connector element, comprising:

a conduit forming a lumen for conveying a flowing medium;

a sealing part moveable relative to the conduit between a closed position and an open position, adapted for sealing the conduit from an ambient atmosphere when in the closed position;

an opening element including an outer socket connector having a diameter that is greater than a diameter of the conduit, the opening element configured to open the sealing part while forming a connection, wherein the opening element prevents the sealing part from contacting the conduit either when in the closed position or in the open position;

a shut-off element adapted for sealing the conduit; and a penetration body movable relative to the shut-off element and adapted for opening the shut-off element when forming the connection.

2. A connector element for connecting a fluid line, preferably a length of tubing, cannulas or catheters to a second connector element, comprising:

a conduit forming a lumen for conveying a flowing medium;

a sealing part moveable relative to the conduit between a closed position and an open position, adapted for sealing the conduit from an ambient atmosphere when in the closed position;

an opening element to open the sealing part while forming a connection, wherein the sealing part does not contact the conduit either when in the closed position or in the open position;

a shut-off element adapted for sealing the conduit; and a penetration body movable relative to the, shut-off element and adapted for opening the shut-off element when forming the connection, wherein the penetration body is disposed within the conduit.

3. The connector element according to claim 2, wherein the penetration body comprises a projection for engaging a second inner socket connector of the second connector element when forming the connection.

4. A method for connecting fluid lines, preferably first and second lengths of tubing, cannulas or catheters, comprising:

attaching a first connector element to the first length and a second connector to the second length;

pushing a housing of the second connector element into a housing of the first connector element, so that an outer socket connector of the first connector element acts on a sealing part of the second connector element to open the sealing part of the second connector element, wherein the sealing part of the second connector is movable relative to a conduit of the second connector and the sealing part of the second connector does not contact the conduit of the second connector either when in the closed or open position, and an outer socket connector of the second connector element acts on a sealing part of the first connector element to open the sealing part of the first connector element, wherein the sealing part of the first connector is movable relative to a conduit of the first connector and the sealing part of the first connector does not contact the conduit of the first connector either when in the closed or open position;

further pushing the housing of the second connector element into the housing of the first connector element, so that a recessed inner socket connector of the first connector element forms a continuous conduit with a recessed inner socket connector of the second connector element; and further pushing the housing of the second connector element into the housing of the first connector element so that a penetration body of the first connector element opens shut off elements of the first and second connector elements.

* * * * *